United States Patent
Herrmann et al.

(10) Patent No.: US 8,772,726 B2
(45) Date of Patent: Jul. 8, 2014

(54) APPARATUS AND METHOD FOR DATA ACQUISITION USING AN IMAGING APPARATUS

(75) Inventors: Christoph Herrmann, Aachen (DE); Michael Overdick, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 455 days.

(21) Appl. No.: 13/203,996

(22) PCT Filed: Feb. 9, 2010

(86) PCT No.: PCT/IB2010/050589
§ 371 (c)(1),
(2), (4) Date: Aug. 31, 2011

(87) PCT Pub. No.: WO2010/109347
PCT Pub. Date: Sep. 30, 2010

(65) Prior Publication Data
US 2011/0315888 A1 Dec. 29, 2011

Related U.S. Application Data

(60) Provisional application No. 61/163,066, filed on Mar. 25, 2009.

(51) Int. Cl.
*G01T 1/20* (2006.01)
*A61B 6/03* (2006.01)
*G01T 1/24* (2006.01)

(52) U.S. Cl.
CPC ............... *G01T 1/249* (2013.01); *A61B 6/032* (2013.01); *G01T 1/2018* (2013.01)
USPC .... 250/361 R; 250/362; 250/368; 250/370.11

(58) Field of Classification Search
USPC .................. 250/361 R, 362, 369, 370.11
See application file for complete search history.

(56) References Cited

U.S. PATENT DOCUMENTS

| 4,052,620 | A | | 10/1977 | Brunnett |
| 4,109,168 | A | * | 8/1978 | Raymond ............... 327/101 |
| 4,893,015 | A | | 1/1990 | Kubierschky et al. |
| 4,965,578 | A | * | 10/1990 | Poujois ............... 341/156 |
| 6,671,345 | B2 | | 12/2003 | Vrettos et al. |
| 7,388,534 | B2 | | 6/2008 | Astley et al. |
| 2002/0141530 | A1 | | 10/2002 | Vrettos et al. |
| 2005/0121617 | A1 | * | 6/2005 | Heismann et al. ....... 250/370.11 |

OTHER PUBLICATIONS

Luhta, R., et al.; A new 2D-tiled detector for multislice CT; 2006; Physics of Medical Imaging; vol. 6142:275-286.

* cited by examiner

*Primary Examiner* — David Porta
*Assistant Examiner* — Mindy Vu

(57) ABSTRACT

A detector tile (116) of an imaging detector array (112) includes a scintillator array (202), a photosensor array (204), which includes a plurality of photosensitive pixels, optically coupled to the scintillator array (202), and a current-to-frequency (I/F) converter (302). The I/F converter (302) includes an integrator (304) that integrates charge output by a photosensitive pixel during an integration period and generates a signal indicative thereof and a comparator (310) that generates a pulse when the generated signal satisfies predetermined criteria during the integration period. A reset device (316) resets the integrator (304) in response to the comparator (310) generating a pulse. Circuitry (320, 324) samples the generated signal at a beginning of the integration period and/or at an end of the integration period and generates quantized digital data indicative thereof. Logic (322) estimates the charge at the input of the integrator (304) based on the generated digital data.

20 Claims, 4 Drawing Sheets

Figure 1:
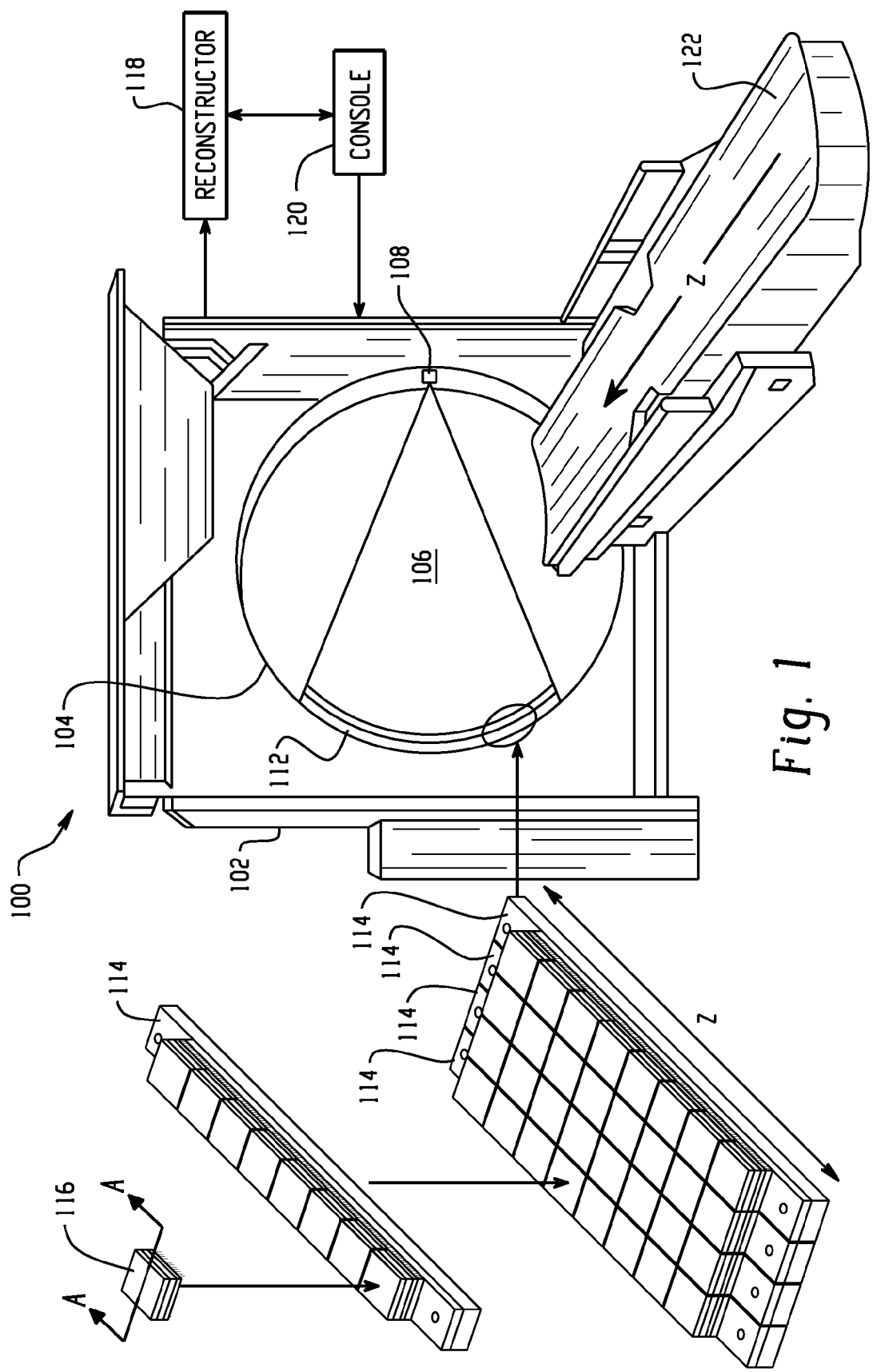

APPARATUS AND METHOD FOR DATA ACQUISITION USING AN IMAGING APPARATUS

CROSS REFERENCE TO RELATED APPLICATIONS

This application claims the benefit of U.S. provisional application Ser No. 61/163,066 filed Mar. 25, 2009, which is incorporated herein by reference.

The following generally relates to data acquisition, and finds particular application to computed tomography (CT). However, it also amenable to other medical imaging applications and to non-medical imaging applications.

A computed tomography (CT) scanner includes an x-ray tube mounted on a rotatable gantry that rotates around an examination region about a longitudinal or z-axis. A detector array subtends an angular arc opposite the examination region from the x-ray tube.

The detector array detects radiation that traverses the examination region and a subject or object therein and generates a signal indicative thereof. A reconstructor reconstructs the signal and generates volumetric image data. The volumetric image data can be processed to generate one or more images.

The detector array generally includes a scintillator array optically coupled to a photosensor array, which is electrically coupled to processing electronics. The scintillator array generates light indicative of radiation impinging thereon, the photosensor array generates an electrical signal indicative of the light, and the processing electronics includes an analog-to-digital (A/D) converter that generates digital data indicative of the detected radiation based on the electrical signal. The digital data is processed to generate the signal reconstructed by the reconstructor.

Unfortunately, as detection technology continues to evolve to more slices, smaller slice widths, lower signals and faster rotation times, noise and/or spatial resolution constraints can limit imaging performance.

Aspects of the present application address the above-referenced matters and others.

According to one aspect, a detector tile of an imaging detector array includes a scintillator array, a photosensor array, which includes a plurality of photosensitive pixels, optically coupled to the scintillator array, and a current-to-frequency (I/F) converter. The I/F converter includes an integrator that integrates charge output by a photosensitive pixel during an integration period and generates a signal indicative thereof and a comparator that generates a pulse when the generated signal satisfies predetermined criteria during the integration period. A reset device resets the integrator in response to the comparator generating a pulse. Circuitry samples the generated signal at a beginning of the integration period and/or at an end of the integration period and generates quantized digital data indicative thereof. Logic estimates the charge at the input of the integrator based on the generated digital data.

The circuitry includes sample and hold circuitry that samples the signal generated by the integrator, and an A/D converter that converts the output of the sample and hold circuitry to the digital data. The logic transitions the A/D converter to a wake state during the integration period when the logic determines that it is unlikely that at least a third predetermined number of pulses will be generated in the integration period. The logic transitions the A/D converter to the idle state during the integration period when at least the third pre-determined number of pulses is generated in the integration period. The logic invokes the A/D converter to sample the signal generated by the integrator at the end of the integration period when less than a fourth predetermined number of pulses is generated in the integration period.

The detector tile further includes a multiplexor that routes the sampled signal to the A/D converter, a second integrator that integrates charge output by a second photosensitive pixel during the integration period and generates a second signal indicative thereof, a second comparator generates a second pulse when the generated second signal exceeds a second predetermined threshold during the integration period, and second sample and hold circuitry that samples the second signal, wherein the multiplexor routes both the sampled signal and the second sampled signal to the A/D converter. The A/D converter is activated if it is likely that either of the comparators is likely to generate less than a fifth predetermined number of pulses during the integration period.

In another embodiment, a method includes integrating input charge during an integration period via an integrator of a current-to-frequency converter. The input charge is indicative of radiation detected by a detector tile of an imaging system. The method further includes generating a pulse with a comparator of the current-to-frequency converter when the integrated charge exceeds a predetermined threshold during the integration period. The method further includes sampling the integrated charge at a beginning of the integration period and/or at an end of the integration period. The method further includes converting the sampled integrated charge into a digital signal. The method further includes estimating the input charge for the integration period based on the sampled integrated charge when less than a predetermined number of pulses are generated during the integration period.

In another embodiment, an imaging system includes a radiation source that generates radiation that traverse an examination region, a detector array that detects radiation that traverses the examination region, and a reconstructor that reconstructs the output of the detector array to generate volumetric image data indicative of the examination region. The detector array includes a plurality of detector tiles, and a detector tile includes a scintillator array and a photosensor array optically coupled to the scintillator array. The photosensor array includes a plurality of photosensitive pixels. The tile also includes a current-to-frequency (I/F) converter having an integrator that integrates charge output by a photosensitive pixel during an integration period and generates a signal indicative thereof and a comparator generates a pulse when the generated signal exceeds a predetermined threshold during the integration period. Circuitry samples the generated signal at a beginning of the integration period and/or at an end of the integration period and generates digital data indicative thereof. Logic estimates the charge at the input of the integrator based on the generated digital data if the comparator generates less than a predetermined number of pulses in the integration period and based on pulses generated by the comparator if the comparator generates at least the predetermined number of pulses in the integration period.

The invention may take form in various components and arrangements of components, and in various steps and arrangements of steps. The drawings are only for purposes of illustrating the preferred embodiments and are not to be construed as limiting the invention.

Figure 2:
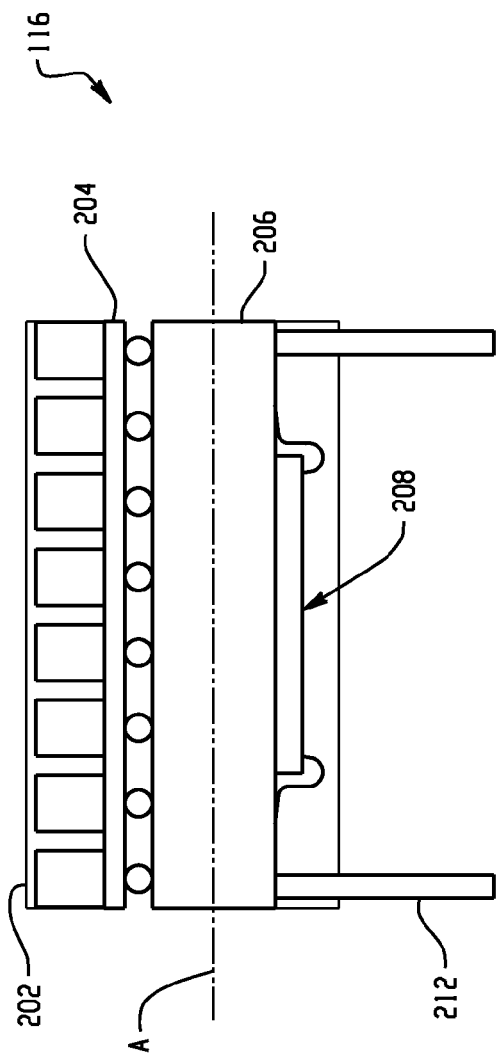
Figure 3:
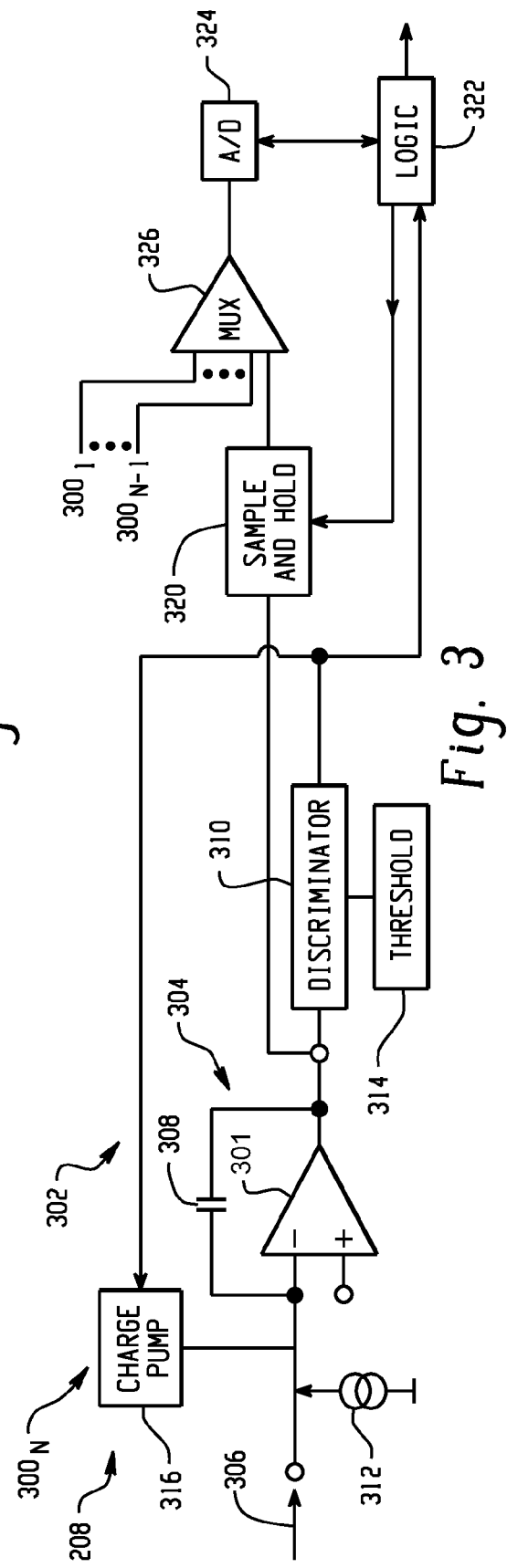
Figure 4:
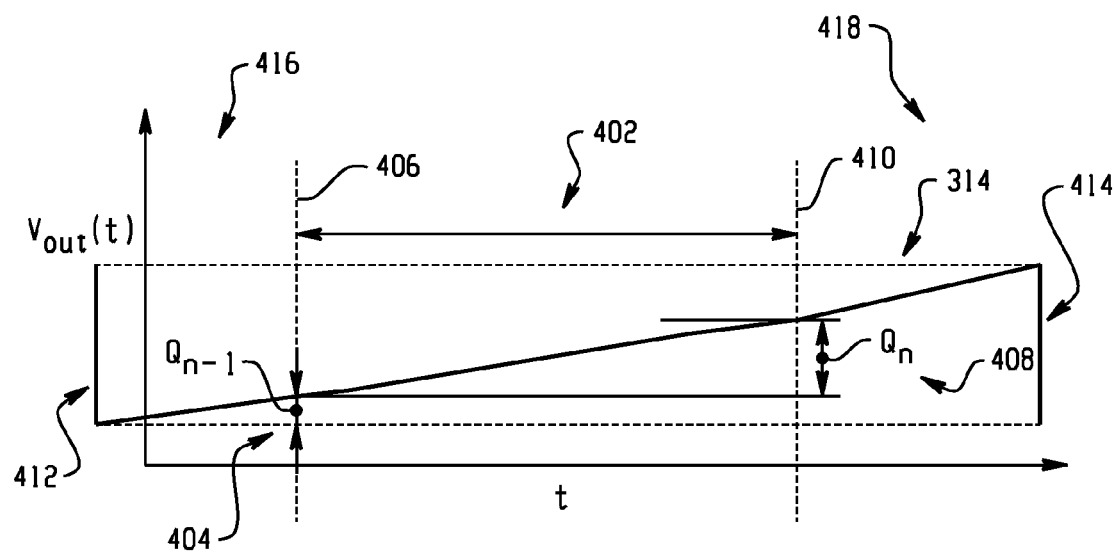
Figure 5:
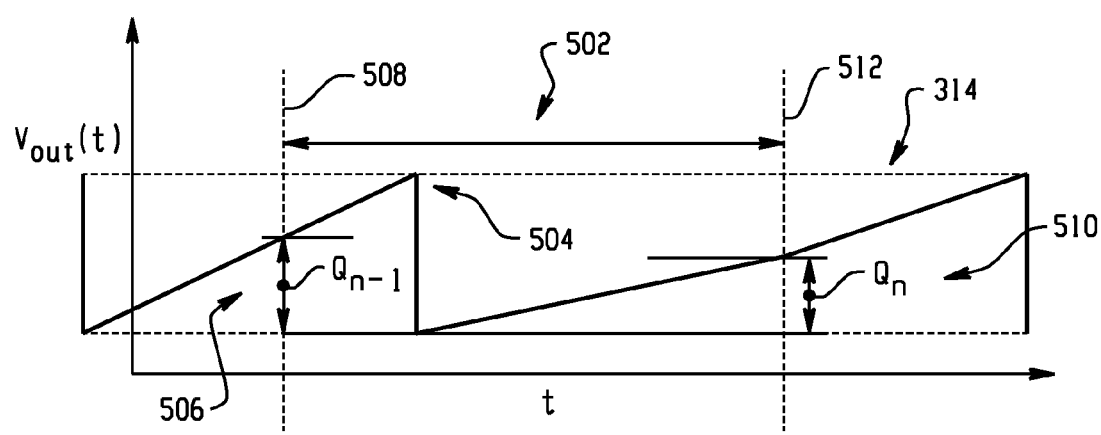

FIG. 1 illustrates an example imaging system.
FIG. 2 illustrates an example detector tile.
FIG. 3 illustrates example detector electronics.
FIGS. 4 and 5 includes diagrams that illustrate example integration periods respectively in which no and one pulse is generated.

Figure 6:
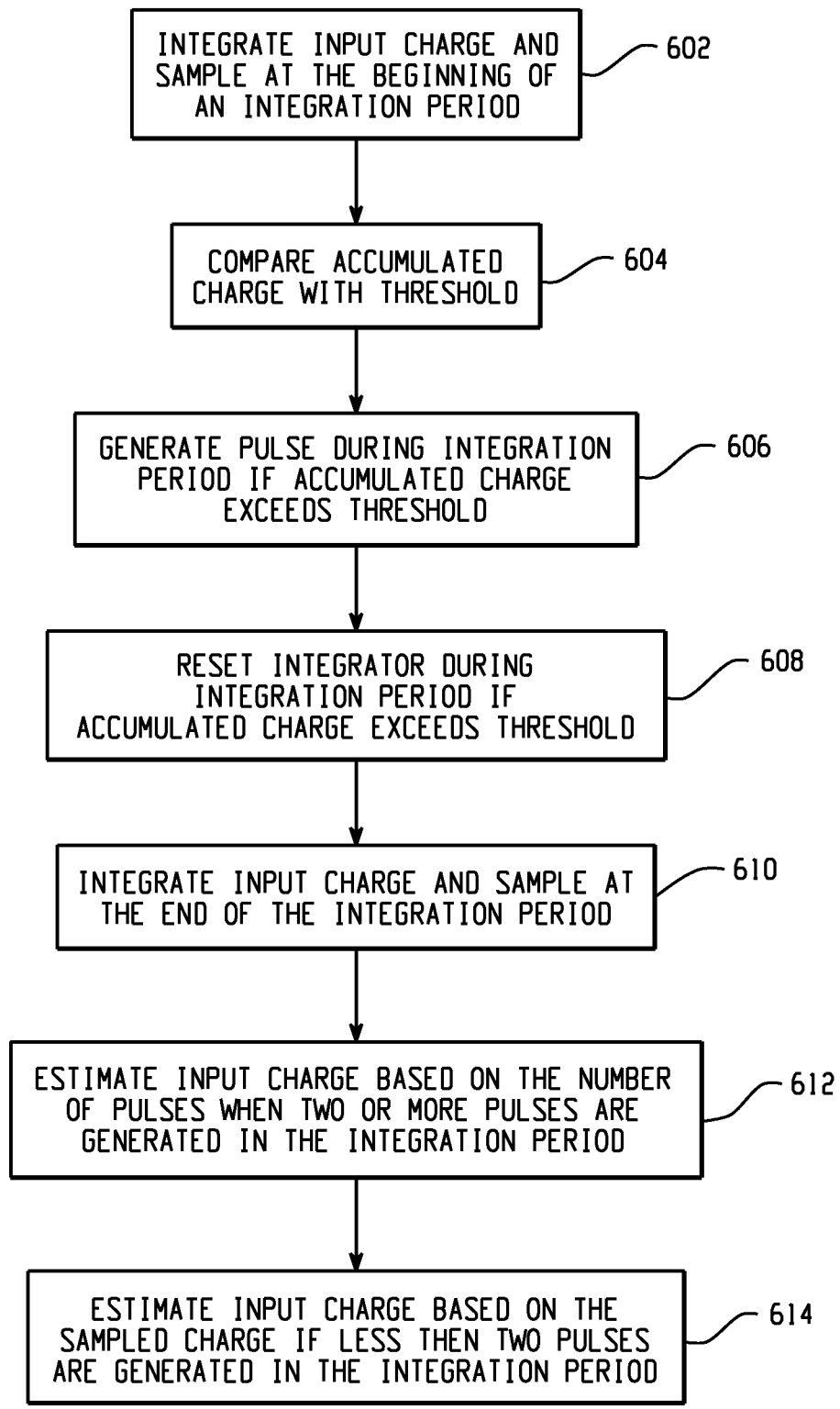

FIG. 6 illustrates an example method.

FIG. 1 illustrates an imaging system 100 such as a computed tomography (CT) scanner. The imaging system 100 includes a generally stationary gantry 102 and a rotating gantry 104. The rotating gantry 104 is rotatably supported by the stationary gantry 102 and rotates around an examination region 106 about a longitudinal or z-axis. A radiation source 108 such as an x-ray tube is supported by the rotating gantry 104 and emits radiation that traverses the examination region 106.

A radiation sensitive detector array 112 subtends an angular arc opposite the radiation sources 108 across the examination region 106 and detects radiation traversing the examination region 106. In the illustrated embodiment, the radiation sensitive detector array 112 includes a plurality of detector modules 114 arranged with respect to each other along a direction transverse to the z-axis. A detector module 114 includes a plurality of detector mosaics or tiles 116 arranged with respect to each other along the z-axis. In one non-limiting instance, the detector array 112 is substantially similar to and/or is based on the detector array described in U.S. Pat. No. 6,510,195B1, filed Jul. 18, 2001, and entitled "Solid State X-Radiation Detector Modules and Mosaics thereof, and an Imaging Method and Apparatus Employing the Same," which is incorporated herein by reference in its entirety. Other detector array arrangements are also contemplated herein.

Turning to FIG. 2, a cross-sectional view of a detector tile 116 along line A-A of FIG. 1 is illustrated. The illustrated tile 116 includes a scintillator array 202 physically and optically coupled to a photosensor array 204, which is electrically coupled to electronics 208 through a substrate 206. Electrical pathways 212 such as connector pins or other electrical pathways carry power supplies and digital I/O signals.

An example of such a tile is described in "A New 2D-Tiled Detector for Multislice CT," Luhta et al., Medical Imaging 2006: Physics of Medical Imaging, Vol. 6142, pp. 275-286 (2006). Other electronics are also contemplated herein.

FIG. 3 illustrates example electronics for an N-th pixel $300_N$ of the tile 116. An analog-to-digital (A/D) converter 302 includes an integrator 304 (an amplifier 306 and an integrating capacitor 308) and a comparator or discriminator 310. In one embodiment, the A/D converter 302 is employed as a current-to-frequency (I/F) converter. An example of such a converter is described in U.S. Pat. No. 6,671,345B2, filed Nov. 7, 2001, and entitled "Data Acquisition for Computed Tomography," which is incorporated herein by reference in its entirety. Another suitable converter is described in U.S. Pat. No. 4,052,620, filed Nov. 28, 1975, and entitled "Data Acquisition for Computed Tomography," both of which are incorporated herein by reference in its entirety. Other converters are also contemplated herein.

When the A/D converter 302 is configured as in I/F converter, the integrator 304 integrates a summation of charge 301 output by the photosensor array 204 and a bias current 312 during an integration period. The discriminator 310 generates a digital pulse when the output of the amplifier 306 satisfies predetermined criteria. In one non-limiting instance, the discriminator 310 compares the output of the amplifier 306 with a threshold 314 during the integration period and generates the digital pulse when the output of the amplifier 306 rises above (or falls below) the threshold 314 (depending on the polarity of the input current and the polarity of the integrator implementation; in the following it is assumed that the integrator 304 generates an increasing output voltage, if the photodiode generates a current). An integrator "resetter" such as a charge pump 316 resets the integrator 304 during the integration period in response to the generation of a digital pulse. The charge pump 316 may also reset the integrator 304 between integration periods. The gain of the integrator 304 may be configured based on reset capacitance of the charge pump 316. Resetting the integrator 304 may include injecting charge into the input of the integrator 304 that cancels the charge at the input of the integrator 304.

Sample and hold circuitry 320 samples the output of the integrator 304 at the beginning and at the end of an integration period, and an A/D converter 324 converts the sampled output to quantized digital data indicative thereof. As described in greater detail below, logic 322 selectively invokes or activates the A/D converter 324. For example, in one non-limiting embodiment the logic 322 activates the A/D converter 324 only if the logic 322 determines that the discriminator 310 did not generate at least two pulses in an integration period. Otherwise, the A/D converter 324 may transition to or be maintained in an idle or sleep state. A multiplexer 326 can be used to route sample and hold circuitry 320 output for a plurality of different pixels 300, ..., $300_{N-1}$ and $300_N$ of the detector tile 116 to the A/D converter 324.

The logic 322 also processes the output of the discriminator 310 and the output of the A/D converter 324. By way of non-limiting example, when at least two pulses are generated by the discriminator 310 during an integration period, the logic 322 processes the at least two pulses. In one instance, such processing includes counting the number of pulses in the integration period and determining a time from a first pulse of the integration period to a last pulse of the integration period. From this data, the logic 322 can generate an output signal having a frequency indicative of the input charge. In one instance, the logic 322 determines the frequency as a function of a ratio of a number of pulses in an integration period to the time between the first and last pulse in the integration period. When less than two pulses are generated by the discriminator 310 during an integration period, the logic 322 processes the output of the A/D converter 324 to estimate the input charge. The logic 322 can also be configured to estimate the charge based on both the number of pulses and the output of the A/D converter 324. This can be done when at least two pulses or another number of pulses are generated by the discriminator 310. In other embodiments, a different number of pulses threshold may be used to facilitate determining whether to process the pulses, the output of the A/D converter 304, or both.

Returning to FIG. 1, a reconstructor 118 reconstructs the signal from the detector array 112 and generates volumetric image data indicative thereof. An image processor or the like can generate one or more images based on the image data. A general purpose computing system serves as an operator console 120. Software resident on the console 120 allows the operator to control the operation of the system 100. A patient support 122, such as a couch, supports an object or subject such as a human patient in the examination region 106.

FIG. 4 shows an example in which no pulse is generated in an integration period, and FIG. 5 shows an example, in which one pulse is generated in an integration period. In both figures, the y-axis represents the output of the integrator 304 (in terms of voltage) and the x-axis represents time. In FIG. 4, the charge accumulated during an integration period 402 corresponds to charge 404 from a beginning 406 of the integration period 402 to charge 408 at an end 410 of the integration period 402. In this example, the accumulated charge does not meet the threshold 314 in the integration period 402. Note that the charge 412 and 414 accumulated in previous and subsequent integration periods 416 and 418 meets the threshold 314.

The sample and hold circuitry 320 samples the accumulated charge 404 at the beginning 406 and the charge 408 at the end 410 of the integration period 402, and the A/D converter 324 converts the charge 404 and 408 to digital signals or a difference between the charge 408 and the charge 404 to a digital signal. In this example, the charge 404 at the beginning 406 of the integration period 402 is used as a reference value or zero level. This may allow for reducing the range of the A/D converter 324 resulting in a finer quantization. The logic 322 processes the output of the A/D converter 324 to estimate the input charge.

In FIG. 5, the charge accumulated during an integration period 502 corresponds to the threshold charge 504 less the charge 506 at a beginning 508 of the integration period 502 and charge 510 at an end 512 of the integration period 502. The sample and hold circuitry 320 samples the charge 506 at the beginning 508 and the charge 510 at the end 512 of the integration period 502, and the A/D converter 324 converts the sampled data to digital signals. The logic 322 estimates the input charge based on the digital signals and the threshold charge.

The following provides a non-limiting example for selectively activating the A/D converter 324 based on the number of pulses generated by the discriminator 310 in an integration period. For this example, assume that the A/D converter 324 is initially in an idle or sleep state. The A/D converter 324 is woken up when there is a predetermined number of pulses such as less than two (none or one (1)) or other number of pulses during a first half of an integration period (IP) ($0 < t \leq t_{IP}/2$). In this example, the A/D converter 324 remains woken if there is no pulse during a second half of the integration period ($\frac{3}{4} t_{IP} < t \leq t_{IP}$) or if there is one (1) pulse during the second half of the integration period and there was no pulse during the first half of the integration period. In other embodiments, the predetermined number of pulses is less or more than two.

As the A/D converter 324 can be employed with a plurality of the pixels $300\text{-}300_N$, including a subset thereof or all, the A/D converter 324 can initially be idle and woken within an integration period when the output of the discriminator 310 for at least one pixel satisfies the activation criteria discussed above or other activation criteria. If the predetermined number of pulses (less than two in this example) are generated in the integration period, the logic 322 invokes the A/D converter 324 to convert the data sampled by the sample and hold circuitry 320. When there is a different predetermined number pulses such as at least two (2) pulses or other number of pulses generated in the integration period, the A/D converter 324 instead transitions back to the idle state. In other embodiments, the different predetermined number of pulses is less or more than two. Selectively activating the A/D converter 324 as such reduces power consumption relative to a configuration in which the A/D converter 324 is always on.

Again, the above ranges for the number of pulses, for which A/D converter is used to digitize the residual signal at a beginning and/or end of an integration period (or not), are provided for explanatory purposes and are not limiting; other ranges are contemplated herein, including more and/or less pulses.

Whether the A/D converter 324 is employed with one of the detector tiles 116 and the size of the A/D converter 324 can be determined based on characteristics of the detector tile 116. For example, for a two hundred and fifty-six (256 channel tile that is more likely to receive smaller signals such as signals that do not result in at least two pulses, e.g., tiles at or nearer a center of the detector array 112, a ten (10), twelve (12) or other bit A/D converter may suffice to process the output of the sample and hold circuitry 302 of the 256 channels.

A non-limiting example of a suitable 10-bit A/D converter has a sampling rate of seventy-five (75) MS/s, a chip area thirty-six hundreths (0.36) millimeter squared ($mm^2$), and a power consumption of less than one hundred and sixty-three (163) milliWatts (mW), and a non-limiting example of a suitable 12-bit A/D converter has a sampling rate of eighty (80) MS/s, a chip area about five tenths (0.5) of a $mm^2$, and a power consumption of less than one hundred and fifty (150) mW. Such converters allow for sufficiently high sample rates and consume a relatively small footprint and low power consumption.

Other A/D converters are also contemplated herein. For a 256 channel tile 116 that is more likely to receive larger signals such as signals that result in at least two pulses, e.g., tiles at or nearer the edges of the detector array 112, an A/D converter 304 may be omitted.

With one 256 channel tile, the recovery time from an idle or sleep state to a wake or active state is about one hundred (100) nanoseconds (ns) plus fifty (50) divided by the sampling rate (Fs). For a sampling rate of twenty (20) MS/s, the recovery time is about two and six tenths (2.6) microseconds (µs), which generally is short enough to switch the A/D converter 324 on after $t_{IP}/2$. With an integration period of 100 µs, there would be plenty of time to wake the A/D converter 324 up, even if none of the 256-channels results in a pulse before $t_{IP}/2$. For a sample rate of about 20 MS/s, power consumption is about seventeen (17) mW for a 12-bit ADC. With such low power consumption, the A/D converter 324 may be activated during an entire integration period rather than based on the criteria discussed in the example herein or other criteria that reduces the duty cycle of the A/D converter 324.

FIG. 6 illustrates a method.

At 602, charge at the input of the integrator 304 at the beginning of an integration period is integrated and sampled.

At 604, as the charge is being integrated during the integration period, the accumulated charge is compared with a predetermined threshold value.

At 606, a pulse is generated during the integration period if the accumulated charge exceeds (or falls below) the predetermined charge threshold.

At 608, the integrator 304 is reset during the integration period if the accumulated charge exceeds (or falls below) the predetermined charge threshold.

At 610, charge at the input of the integrator 304 at the end of the integration period is also integrated and sampled.

At 612, if at least two (or another predetermined number of) pulses are generated for the integration period, the input charge is estimated based on the number of pulses in the integration period.

At 614, if less than two (or another predetermined number of) pulses are generated for the integration period, the input charge is estimated based on the charge sampled at the beginning and at the end of the integration period.

Acts 602 to 614 are repeated for one or more integration periods.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A detector tile of an imaging detector array, comprising:
   a scintillator array;
   a photosensor array optically coupled to the scintillator array, wherein the photosensor array includes a plurality of photosensitive pixels;

a current-to-frequency (I/F) converter, including:
   an integrator that integrates charge output by a photosensitive pixel during an integration period and generates a signal indicative thereof; and
   a comparator that generates a pulse when the generated signal satisfies predetermined criteria during the integration period;
a reset device that resets the integrator in response to the comparator generating a pulse;
circuitry that samples the generated signal at a beginning of the integration period and/or at an end of the integration period and generates quantized digital data indicative thereof; and
logic that estimates the charge at the input of the integrator (304) based on the generated digital data if the comparator generates less than a first predetermined number of pulses in the integration period.

2. The detector tile of any of claim 1, wherein the logic estimates the input charge based on the generated digital data and the pulses generated by the comparator.

3. The detector tile of claim 2, wherein the logic estimates the input charge based on the pulses if the comparator generates at least a second predetermined number of pulses in the integration period.

4. The detector tile of any of claim 1, wherein the circuitry includes:
   sample and hold circuitry that samples the signal generated by the integrator; and
   an A/D converter that converts the output of the sample and hold circuitry to the digital data.

5. The detector of claim 4, wherein the A/D converter transitions to or is maintained in an idle state at the beginning of the integration period.

6. The detector tile of claim 4, wherein the logic transitions the A/D converter to a wake state during the integration period when the logic determines that at least a third predetermined number of pulses will be generated in the integration period.

7. The detector tile of claim 6, wherein the logic transitions the A/D converter to the idle state during the integration period when at least the third pre-determined number of pulses is generated in the integration period.

8. The detector tile of claim 4, wherein the logic invokes the A/D converter to sample the signal generated by the integrator at the end of the integration period when less than a fourth pre-determined number of pulses is generated in the integration period.

9. The detector tile of claim 1, further including a multiplexor that routes the sampled signal to the A/D converter.

10. The detector tile of claim 9, further including:
   a second integrator that integrates charge output by a second photosensitive pixel during the integration period and generates a second signal indicative thereof; and
   a second comparator generates a second pulse when the generated second signal exceeds a second predetermined threshold during the integration period; and
   second sample and hold circuitry that samples the second signal, wherein the multiplexor routes both the sampled signal and the second sampled signal to the A/D converter.

11. The detector of claim 10, wherein the A/D converter is activated if it is determined that either of the comparators will generate less than a fifth predetermined number of pulses during the integration period.

12. A method, comprising:
integrating input charge during an integration period via an integrator of a current-to-frequency converter, wherein the input charge is indicative of radiation detected by a detector tile of an imaging system;
generating a pulse with a comparator of the current-to-frequency converter when the integrated charge exceeds a predetermined threshold during the integration period;
sampling the integrated charge at a beginning of the integration period and at an end of the integration period;
converting the sampled integrated charge into a digital signal; and
estimating the input charge for the integration period based on the sampled integrated charge when less than a predetermined number of pulses is generated during the integration period.

13. The method of claim 12, further including estimating the input charge for the integration period based on generated pulses when at least the predetermined number of pulses is generated during the integration period.

14. The method of claim 12, further including resetting the integrator during the integration period in response to generating the pulse.

15. The method of claim 12, further including employing the charge sampled at the beginning of the integration period as reference charge to zero level for the estimated input charge.

16. The method of claim 12, wherein the sampled integrated charge is converted to the digital signal with an analog-to-digital converter, and further maintaining the analog-to-digital converter in an idle state at the beginning of the integration period.

17. The method of claim 16, further transitioning the analog-to-digital converter to a wake state during the integration period.

18. The method of claim 17, further transitioning the analog-to-digital converter back to the idle stated during the integration period if at least two pulses are generated during the integration period.

19. The method of claim 16, further invoking the analog-to-digital converter to convert the sampled integrated charge at the end of the integration period if less than the predetermined number of pulses is generated during the integration period.

20. An imaging system, comprising:
a radiation source that generates radiation that traverse an examination region;
a detector array that detects radiation that traverses the examination region; and
a reconstructor that reconstructs the output of the detector array to generate volumetric image data indicative of the examination region;
wherein the detector array includes a plurality of detector tiles, and a detector tile includes:
a scintillator array;
a photosensor array optically coupled to the scintillator array, wherein the photosensor array includes a plurality of photosensitive pixels;
a current-to-frequency (I/F) converter, including:
   an integrator that integrates charge output by a photosensitive pixel during an integration period and generates a signal indicative thereof; and
   a comparator generates a pulse when the generated signal exceeds a predetermined threshold during the integration period;
   circuitry that samples the generated signal at a beginning of the integration period and at an end of the integration period and generates digital data indicative thereof; and logic that estimates the charge at the input of the integrator based on the generated digital data if the comparator generates less than a predetermined number of pulses in the integration period and based on pulses generated by the comparator if the comparator generates at least the predetermined number of pulses is in the integration period.

* * * * *